(12) United States Patent
Kim et al.

(10) Patent No.: US 11,883,646 B2
(45) Date of Patent: Jan. 30, 2024

(54) MICROCURRENT PATCH

(71) Applicant: VITZROCELL CO. LTD., Dangjin-si (KR)

(72) Inventors: Nam In Kim, Gwangju (KR); Chae Bong Lee, Dangjin-si (KR); Aram Choi, Dangjin-si (KR); Jong Jin Park, Dangjin-si (KR); Tae Jin Bang, Dangjin-si (KR)

(73) Assignee: VITZROCELL CO. LTD., Dangjin-si (KR)

(*) Notice: Subject to any disclaimer, the term of this patent is extended or adjusted under 35 U.S.C. 154(b) by 0 days.

(21) Appl. No.: 17/632,341

(22) PCT Filed: Jul. 31, 2020

(86) PCT No.: PCT/KR2020/010116
§ 371 (c)(1),
(2) Date: Feb. 2, 2022

(87) PCT Pub. No.: WO2021/025381
PCT Pub. Date: Feb. 11, 2021

(65) Prior Publication Data
US 2022/0280778 A1 Sep. 8, 2022

(30) Foreign Application Priority Data
Aug. 2, 2019 (KR) .................. 10-2019-0094371

(51) Int. Cl.
*A61N 1/04* (2006.01)
*H01B 3/42* (2006.01)

(52) U.S. Cl.
CPC ............ *A61N 1/0496* (2013.01); *H01B 3/427* (2013.01)

(58) Field of Classification Search
CPC .. A61N 1/0496; A61N 1/205; A61N 1/36014; A61N 1/0492; A61N 1/02;
(Continued)

(56) References Cited

U.S. PATENT DOCUMENTS 6,661,161 B1 * 12/2003 Lanzo ..................... A61B 7/00
310/334
9,814,877 B2 11/2017 Moon
(Continued)

FOREIGN PATENT DOCUMENTS

JP   2003-250913 A   9/2003
JP   2016-516549 A   6/2016
(Continued)

OTHER PUBLICATIONS

International Search Report dated Dec. 7, 2020, for corresponding International Patent Application No. PCT/KR2020/010116.
(Continued)

*Primary Examiner* — Ankit D Tejani
*Assistant Examiner* — Joshua Brendon Solomon
(74) *Attorney, Agent, or Firm* — Hauptman Ham, LLP

(57) ABSTRACT

The present invention relates to a microcurrent patch having a small battery and a circuit unit that are arranged on a substrate and are covered with a glue layer so as to be formed as one body on the substrate, and thus the present invention is easy to use, improves productivity, and has excellent flexibility, thereby facilitating attachment to a human body having many curves, and adjusting the amount of current flowing through the patch according to the linear width of the circuit unit or the number of holes in the glue layer.

6 Claims, 7 Drawing Sheets

(58) Field of Classification Search
CPC . A61N 1/025; A61N 1/04; A61N 1/36; H01B 3/427
See application file for complete search history.

(56) References Cited

U.S. PATENT DOCUMENTS

| | | | |
|---|---|---|---|
| 10,821,297 B2 | 11/2020 | Binner et al. | |
| 2009/0076363 A1* | 3/2009 | Bly | A61B 5/02055 600/372 |
| 2013/0338472 A1* | 12/2013 | Macia Barber | A61B 5/02055 174/255 |
| 2015/0165186 A1* | 6/2015 | Dar | A61N 1/0492 607/152 |
| 2015/0173639 A1* | 6/2015 | Ichida | A61N 1/0472 600/397 |
| 2015/0374972 A1 | 12/2015 | Lee | |
| 2016/0058998 A1 | 3/2016 | Skiba et al. | |
| 2016/0058999 A1 | 3/2016 | Skiba | |
| 2016/0059009 A1 | 3/2016 | Skiba et al. | |
| 2016/0256686 A1 | 9/2016 | Moon | |
| 2017/0087350 A1 | 3/2017 | Skiba | |
| 2018/0093106 A1 | 4/2018 | Binner et al. | |
| 2018/0099143 A1 | 4/2018 | Kim et al. | |
| 2018/0263525 A1* | 9/2018 | Liao | A61B 5/6843 |
| 2020/0008299 A1* | 1/2020 | Tran | H05K 1/0386 |
| 2020/0222687 A1 | 7/2020 | Skiba et al. | |
| 2022/0168559 A1 | 6/2022 | Skiba et al. | |

FOREIGN PATENT DOCUMENTS

| | | |
|---|---|---|
| KR | 10-1048506 B1 | 7/2011 |
| KR | 10-1423241 B1 | 7/2014 |
| KR | 10-1473433 B1 | 12/2014 |
| KR | 10-2015-0062905 A | 6/2015 |
| KR | 10-2019-0061033 A | 6/2019 |
| KR | 10-2020-0034317 A | 3/2020 |
| WO | 2008/032291 A2 | 3/2008 |

OTHER PUBLICATIONS

Written Opinion dated Dec. 7, 2020, for corresponding International Patent Application No. PCT/KR2020/010116.
Extended European Search Report dated Aug. 4, 2022, for corresponding European Patent Application No. 20849880.8 (7 pages).

* cited by examiner

MICROCURRENT PATCH

CROSS-REFERENCE TO RELATED APPLICATIONS

The present application is a national stage filing under 35 U.S.C. § 371 of PCT application number PCT/KR2020/010116, filed on Jul. 31, 2020, which is based upon and claims the benefit of priorities to Korean Patent Application No. 10-2019-0094371, filed on Aug. 2, 2019, in the Korean Intellectual Property Office, which are incorporated herein in their entireties by reference.

TECHNICAL FIELD

The present disclosure relates to a microcurrent patch. More specifically, the present disclosure relates to a microcurrent patch in which a small-sized battery and a circuit are disposed on the base and the small-sized battery and the circuit on the base are covered with a glue layer, such that when the patch is attached to a human body, microcurrent flows through skin.

DESCRIPTION OF RELATED ART

Recently, it has been reported that various and positive body signals are expressed when a microcurrent flows through the human body. Applying microcurrent to the human body is known to have effects such as activating metabolism and blood circulation, improving body functions such as increasing immunity, pain relief, cell regeneration and hormone secretion promotion. Thus, products using various types of microcurrents are disclosed.

Most of these products have a disadvantage that they are bulky and it is inconvenient to use them as each product are divided into a pad part attached to the human body and a battery connected thereto.

In order to solve this problem, Korean Patent No. 10-1423241 discloses a microcurrent generating patch.

This document proposes a configuration in which a first metal and a second metal having different materials are respectively attached to both sides of an adhesive layer of the patch so that microcurrent is generated in the patch when the patch is attached to the body.

However, in the document as described above, an electrode made of a metal component interacts with a human body fluid acting as an electrolyte to generate a current. Flexibility is remarkably reduced and current is lost.

DISCLOSURE

Technical Purposes

Accordingly, the disclosure has been made in consideration of the problem of the prior art as described above. Thus, a purpose of the present disclosure is to provide a microcurrent patch in which a small-sized battery and a circuit are disposed on a base, and the small-sized battery and the circuit on the base are covered with a glue layer to form a singe body, and thus it is convenient to use the patch.

In addition, another purpose of the present disclosure is to provide a microcurrent patch that is easily attached to a curved human body because the patch has excellent flexibility.

In addition, another purpose of the present disclosure is to provide a microcurrent patch capable of controlling an amount of current flowing through the patch based on a linear width of the circuit or the number of holes in the glue layer.

Technical Solutions

A microcurrent patch according to the present disclosure includes: a base made of a polymer film; a small-sized battery disposed on the base to generate current; a circuit disposed on the base and connected to the small-sized battery, wherein the circuit are disposed in two regions so that the current flows in the circuit; and a glue layer disposed on the base and constructed to cover the small-sized battery and the circuit, wherein the glue layer has a plurality of holes defined therein overlapping the circuit.

The base includes one or more components from a group consisting of polyethylene naphthalate (PEN), and polyethylene terephthalate (PET).

The small-sized battery includes at least two small-sized batteries arranged in a parallel manner and disposed on the base. The small-sized battery includes at least two small-sized batteries arranged in a series manner and disposed on the base.

The circuit is electrically connected to the small-sized battery, wherein the circuit is divided into a circuit portion connected to a positive terminal of the small-sized battery and a circuit portion connected to a negative terminal thereof.

The circuit has a structure in a form of a mesh intersecting with each other.

The circuit is formed in a linear shape, and a linear width of the linear shape is in a range of 0.01 to 10 mm.

The circuit includes one or more components selected from a group consisting of carbon, nickel, silver, aluminum, copper, and gold.

Each of both opposing faces of the glue layer is made of an adhesive material and has insulation ability.

The glue layer is made of acrylate, and has a thickness of 0.01 μm to 1,000 μm.

Technical Effects

According to the microcurrent patch of the present disclosure, the small-sized battery and the circuit are disposed on the base, and the small-sized battery and the circuit on the base are covered with the glue layer to form a single body. Thus, it is convenient to use the patch. This increases productivity of the patch, thereby improving marketability of the product.

In addition, the microcurrent patch according to the present disclosure has excellent flexibility, and may be easily attached to a curved human body, thereby providing use convenience.

In addition, the microcurrent patch may control the amount of current flowing through the patch based on the linear width of the circuit or the number of holes in the glue layer. Further, a total voltage and a total capacity of the batteries may be easily adjusted based on the number of series or parallel connected small-sized batteries.

DETAILED DESCRIPTIONS

Figure 1:
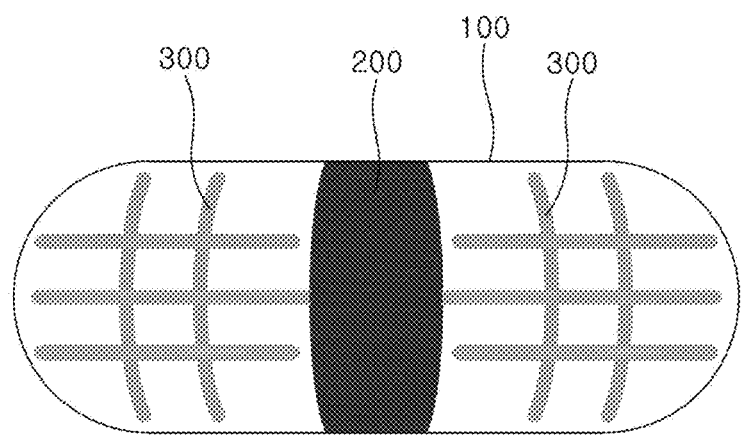
FIG. 1 is a plan view of a microcurrent patch according to the present disclosure.

Hereinafter, an embodiment of the present disclosure will be described with reference to the accompanying drawings. However, the embodiment of the present disclosure may be modified in various other forms, and the scope of the present disclosure is not limited only to the embodiments described below. Shapes and sizes of elements in the drawings may be exaggerated for a clearer illustration, and the same reference numerals in the drawings are allocated to the same elements.

A microcurrent patch according to the present disclosure is attached to the human body and is configured to generate microcurrent and flow the same through the skin, and is composed of a base 100, a small-sized battery 200, a circuit 300, and a glue layer 400.

As shown in FIG. 1, the base 100 is made of a soft and thin polymer film, and not only serves as a base on which the small-sized battery 200 and the circuit are printed, but also serves as a packaging material for the small-sized battery 200. The base is made of a material having water-blocking ability and non-harmful to the human body.

Accordingly, the base 100 preferably includes least one component from a group consisting of polyethylene naphthalate (PEN), and polyethylene terephthalate (PET).

The small-sized battery 200 disposed on the base 100 may be disposed in a central location of the base 100 and in a form of a single battery and may be manufactured by a printing method.

A typical electric capacity of the small-sized battery 200 is between 0.01 mAh and 300 mAh. The battery 200 and the base 100 constitute a single body.

The circuit 300 is formed in two areas respectively on both opposing sides of the small-sized battery 200 by a printing method, and is connected to a positive electrode and a negative electrode of the small-sized battery 200.

While the circuit 300 in one area is connected to the positive electrode of the small-sized battery 200, the circuit 300 in the other area is connected to the negative electrode of the small-sized battery 200.

The circuit 300 may be preferably formed in a structure that is linear and crosses each other in a net shape so that current flows smoothly over a large area of the skin. The two areas of the circuit 300 may be formed in a planar shape.

A linear width of the circuit 300 is preferably 0.01 to 10 mm. The circuit 300 preferably includes one or more components selected from a group consisting of conductive components such as carbon, nickel, silver, aluminum, copper, and gold.

In this connection, the circuit 300 is not necessarily formed in a linear form, but may be formed in a planar shape having a certain area size.

The small-sized battery 200 and the circuit 300 as described above may be manufactured by a vacuum deposition process including a coating method and a sputtering method rather than the printing method.

Figure 2:
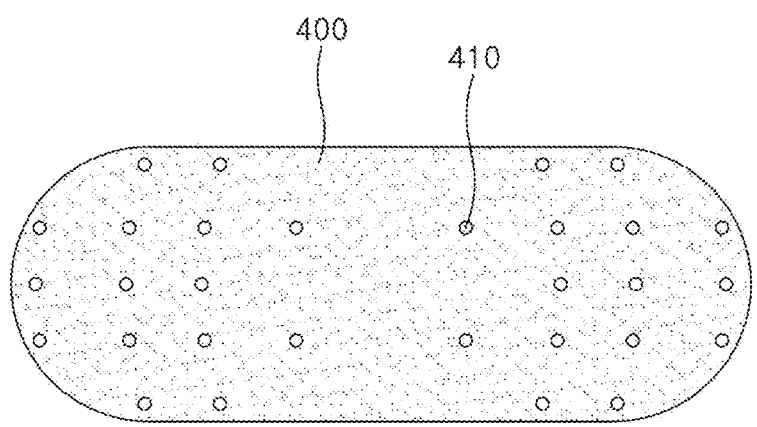
FIG. 2 is a plan view showing a shape of a glue layer according to the present disclosure.

As shown in FIG. 2, both opposing faces of the glue layer 400 are made of an adhesive material having an insulation ability.

One face of the glue layer 400 is configured to cover an entirety of the base 100 including the small-sized battery 200 and the circuit 300, and the other face thereof is attached to the skin of the human body. Therefore, the glue layer 400 is formed to have the same size as that of the base 100, and may be made of an acrylate based material which may adhere well to a curved human skin and may not cause skin troubles.

A plurality of holes 410 extend through the glue layer 400. The holes 410 are positioned to coincide with a position of the circuit 300 and serve as a passage through which an electric current flows between the skin and the circuit 300 when the patch is attached to the skin of the human body.

In this connection, the number and diameters of the holes 410 will be determined in relation to a thickness of the glue layer 400 and a width of the circuit 300.

Figure 3:
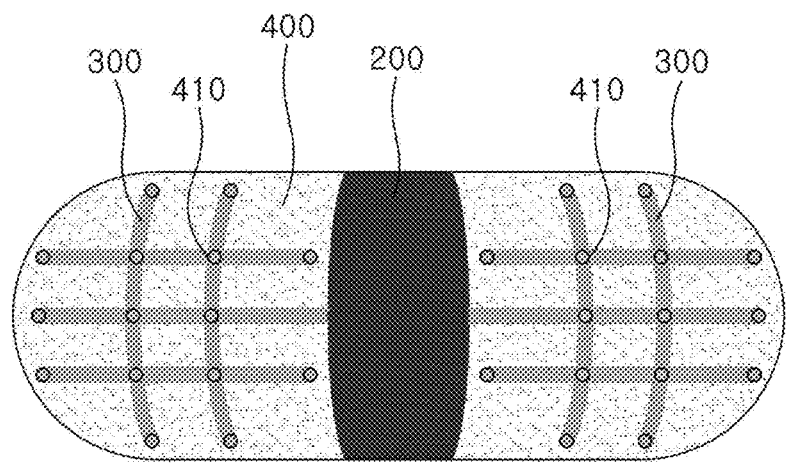
FIG. 3 is a plan view showing a state in which a small-sized battery and a circuit are disposed on a base and are covered with a glue layer according to the present disclosure.

As shown in FIG. 3, when the small-sized battery 200 and the circuit 300 arranged on the base 100 are covered with the glue layer 400, the positions of the number of holes 410 formed in the glue layer 400 overlap the circuit 300.

Since the glue layer 400 acts as an insulator, the small-sized battery 200 still maintains an open circuit state while the glue layer completely covers the circuit 300 connected to the small-sized battery 200.

When the microcurrent patch according to the present disclosure having the glue layer 400 is attached to the human body, a closed circuit is formed through the holes 410 of the glue layer 400 and the small-sized battery 200 is brought into a discharged state using the human skin as a medium.

When the microcurrent patch is attached to the human skin, the amount of current flowing through the human body is closely related to the internal resistance and voltage of the small-sized battery 200, the shape and electrical resistance of the circuit 300, the number and sizes of the holes 410 in the glue layer 400, and the human condition of the individual.

Since the circuit 300 divided into the two regions on the microcurrent patch is completely covered with the glue layer 400, the glue layer 400 must have insulation ability. If the glue layer 400 becomes conductive, the small-sized battery 200 of the microcurrent patch starts being discharged as soon as the patch has been assembled, and the small-sized battery 200 is completely discharged before the path is attached to the body, and thus the battery may not work.

Figure 4:
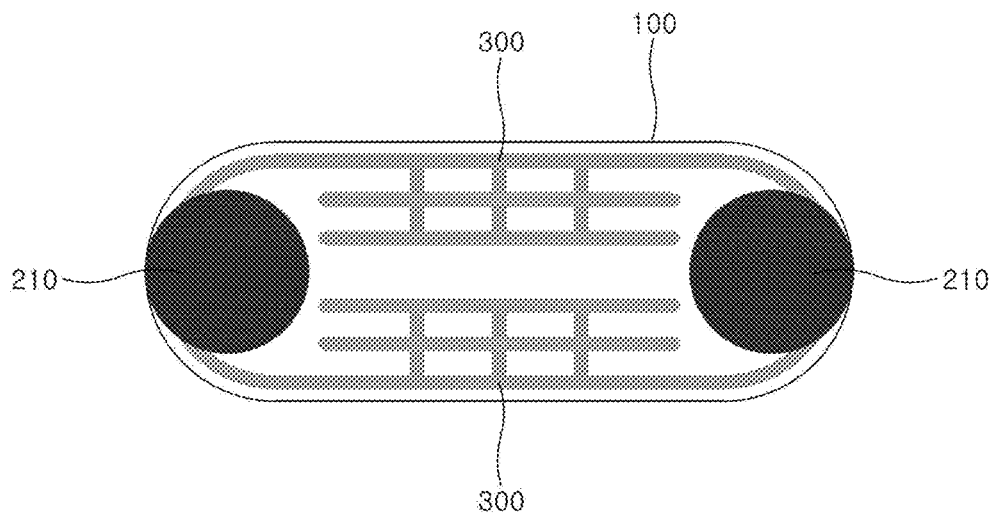
FIG. 4 is a plan view showing a microcurrent patch in a state in which small-sized batteries are arranged in parallel to each other according to the present disclosure.
Figure 5:
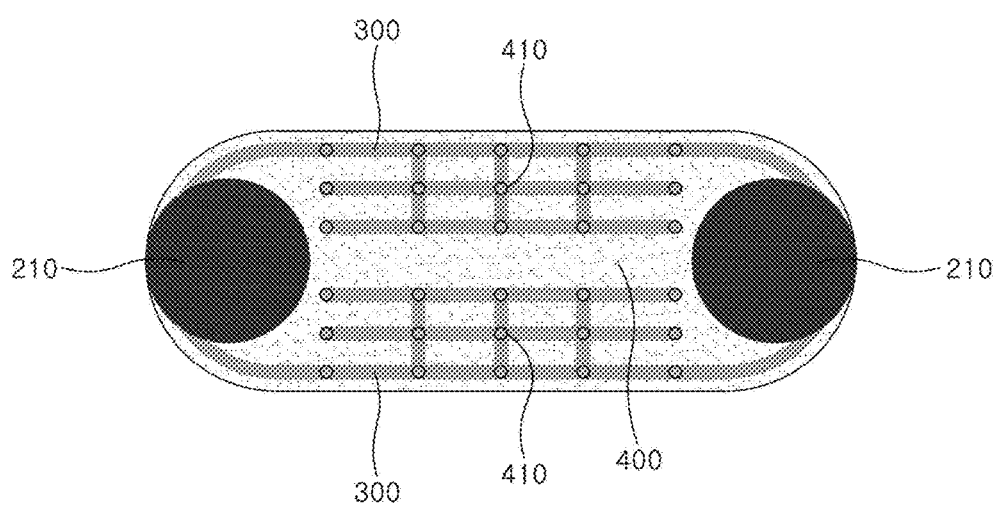
FIG. 5 is a plan view showing a state in which small-sized batteries arranged in parallel to each other and the circuit are disposed on a base and are covered with a glue layer according to the present disclosure.

As shown in FIG. 4 to FIG. 5, the small-sized batteries 210 may be connected to each other in a parallel manner and may be disposed on the base 100.

As the area of the microcurrent patch increases, it is easy to create a large resistance gradient on the circuit 300. At this time, an intensive current flow is generated in the vicinity of the small-sized battery 210. To prevent this phenomenon, a microcurrent patch with a parallel structure is needed.

When the small-sized batteries 210 are connected to each other in a parallel manner, a total capacity of the small-sized batteries 210 may be doubled, but the voltage thereof is the same.

In this connection, it is self-evident that the circuit 300 connecting the small-sized batteries 210 to each other is divided into two regions. The glue layer 400 covers the small-sized batteries 210 and the circuit 300, while the plurality of holes 410 overlap the circuit 300 formed in a mesh structure.

To increase an amount of the current flowing through the skin of the human body, the internal resistance of the small-sized battery, the electrical resistance of the circuit, and the contact resistance between the human skin and the circuit 300 may be reduced or two small-sized batteries may be connected to each other in a series manner to increase the voltage.

Figure 6:
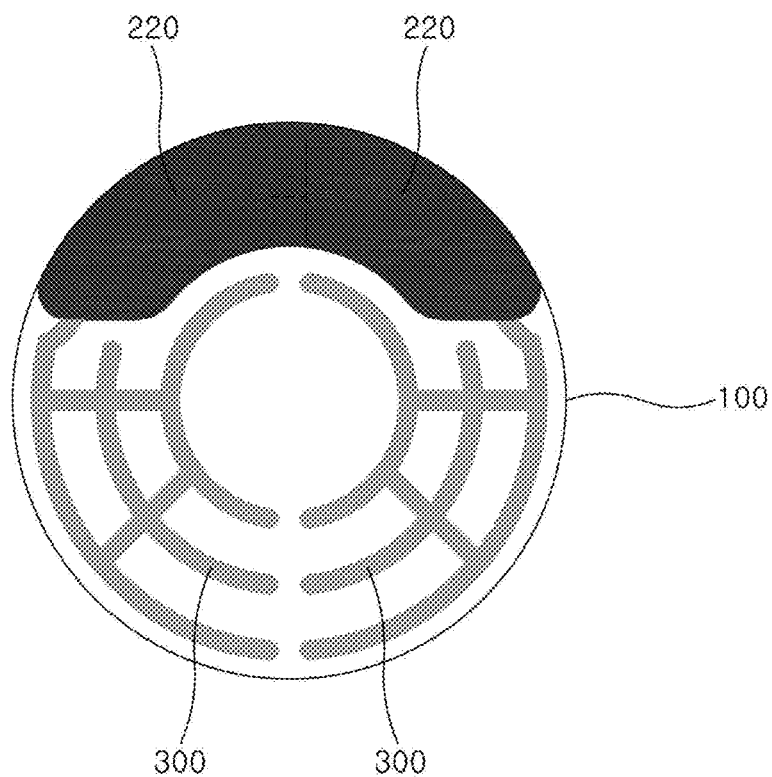
FIG. 6 is a plan view showing a microcurrent patch in a state in which small-sized batteries are arranged in series with each other according to the present disclosure.
Figure 7:
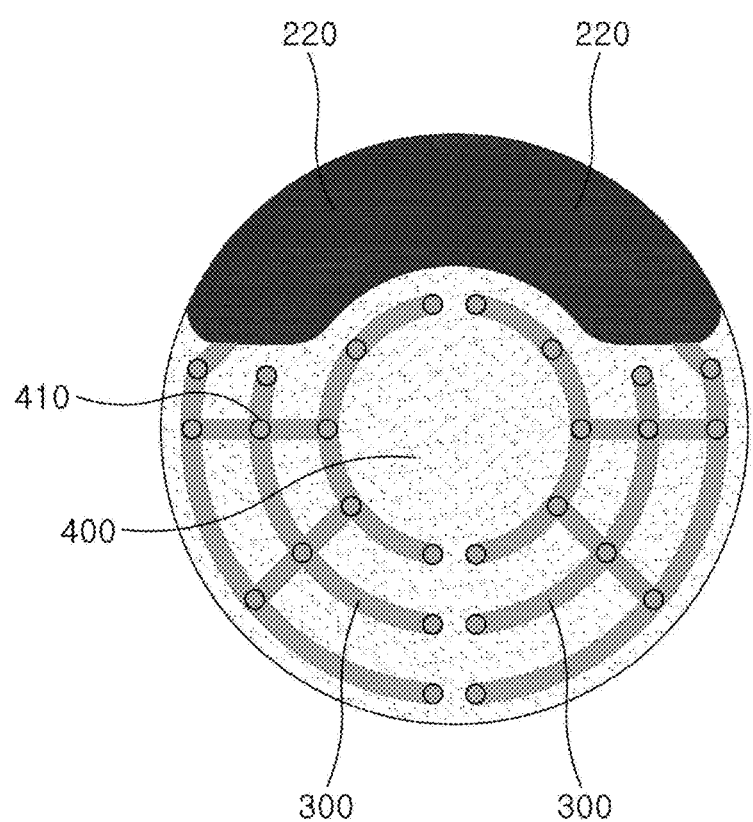
FIG. 7 is a plan view showing a state in which small-sized batteries arranged in series with each other and a circuit are disposed on a base and are covered with a glue layer according to the present disclosure.

As shown in FIG. 6 to FIG. 7, the small-sized batteries 220 may be connected to each other in the series manner and may be disposed on the base 100.

Connecting the small-sized batteries 220 to each other in the series manner has the effect of doubling the amount of the flowing current. When the microcurrent patch equipped with the small-sized battery 220 is attached to a thick skin layer of the human skin, effectiveness of the microcurrent may increase.

As shown in FIG. 1 to FIG. 7, the microcurrent patch may achieve the desired effect by arranging a number of small-sized batteries as well as controlling the shape in the desired manner.

[Test]

Figure 8:
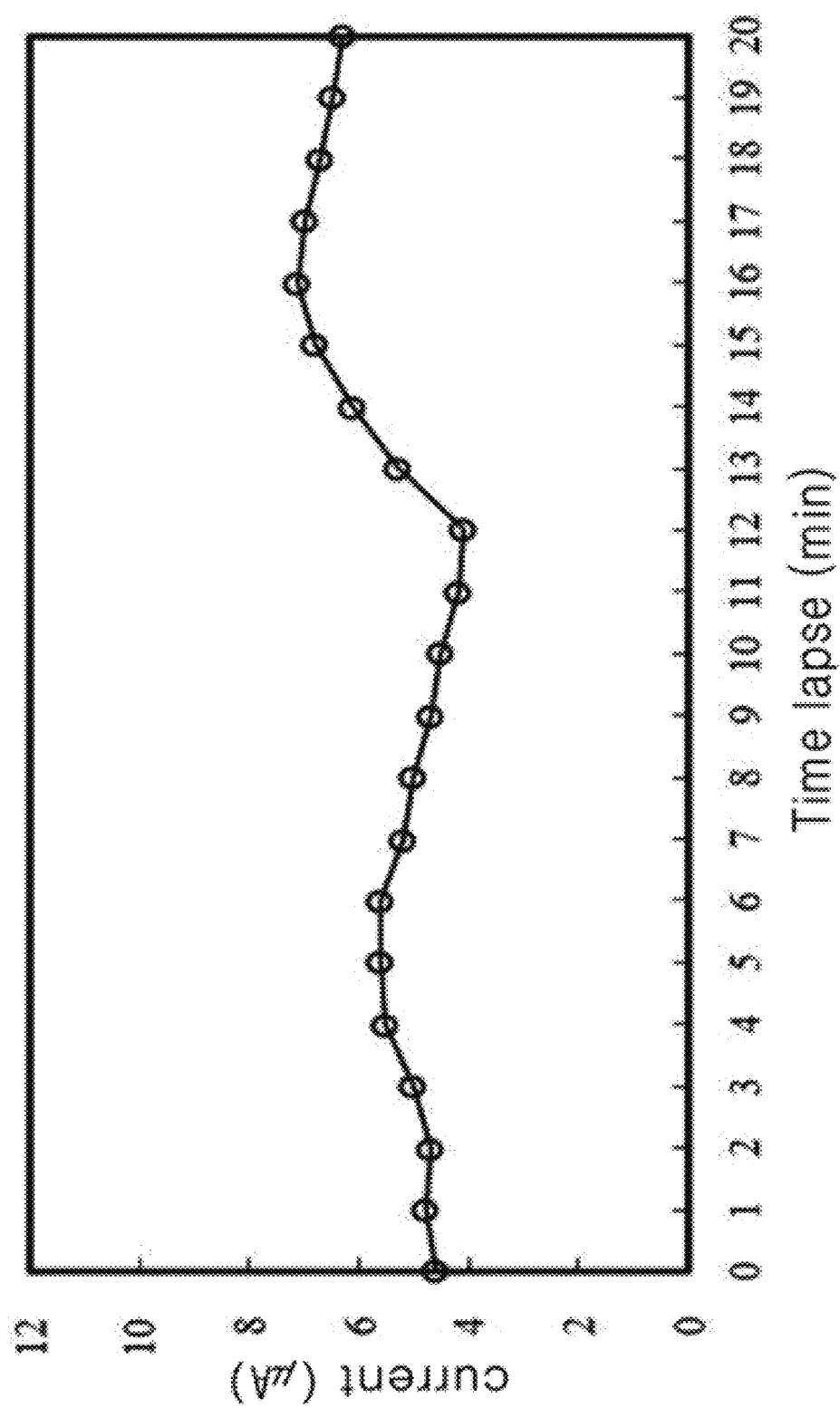
FIG. 8 to FIG. 10 are graphs showing test results of the microcurrent patch as manufactured according to the present disclosure.

FIG. 8 is a test result when the microcurrent patch manufactured according to the present disclosure is attached to the human body.

The microcurrent patch had a circular shape with a diameter of 60 mm, and a small-sized battery of 1.5 V was mounted thereon.

After attaching the microcurrent patch to a wrist, we observed the current flowing through the skin for 20 minutes using an ammeter. It is identified that 4 to 8 microamperes (µA) flows.

Figure 9:
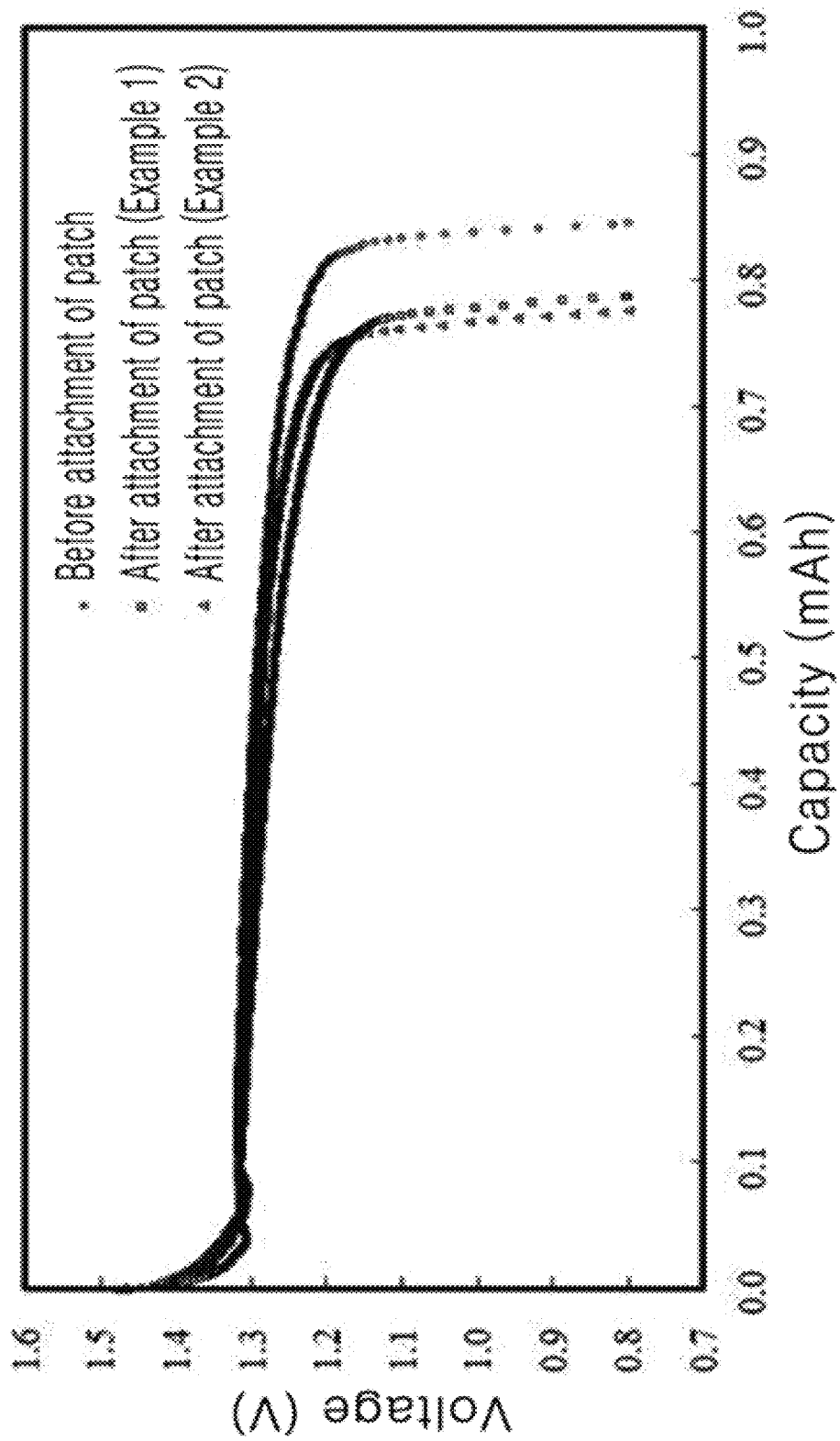

FIG. 9 shows a calculation result of an average current flowing while the patch is attached to the body by attaching the microcurrent patch to the skin and, after a certain period of time, removing the patch therefrom, and measuring the capacity of the small-sized battery and comparing the measured capacity with a capacity of the small-sized battery in the patch before the attachment.

Two people participated in the test, and a patch attachment site was an inner face of the armpit, and the voltage of the small-sized battery was 1.5V.

The patch was applied to a subject in Example 1 for 48 hours. The patch was applied to a subject in Example 2 for 72 hours. Then, the patch was removed therefrom. A capacity of the small-sized battery of the patch was measured.

It was identified that under decrease in the capacity of the small-sized battery, in Example 1, an average of 1.2 microamperes µA flowed, and in Example 2 in which the patch was attached for 72 hours, about 1 µA flowed.

Figure 10:
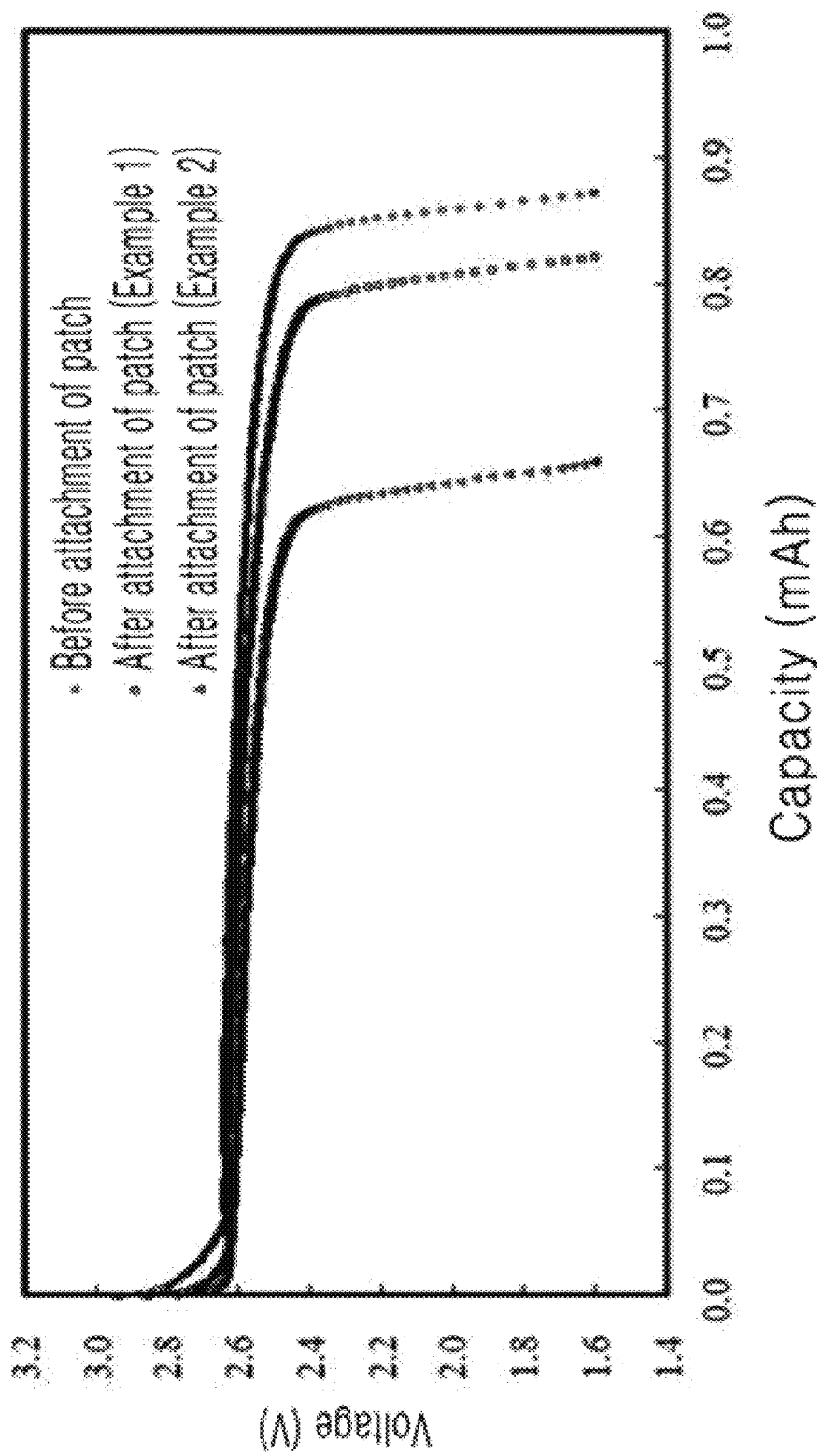

In addition, FIG. 10 identifies the effect of the voltage of the small-sized battery mounted on the microcurrent patch on the amount of the skin current by attaching a microcurrent patch in which two small-sized batteries are connected to each other in series to the body, and after a certain period of time has elapsed, removing the patch therefrom such that the small-sized battery was discharged.

Two people participated in the test, and the patch attachment site was an inner face of the thigh.

The patch attachment time duration was the same and thus 24 hours for two peoples. In Example 1, an average of 2.1 µA flowed over 24 hours, and in Example 2, 8.8 µA flowed over 24 hours, resulting in a higher current than that in Example 1. Through the above test, the current flowing according to the state of the body and the voltage of the battery at the time of the test had different values for different persons who participated in the test.

The present disclosure is not limited to the above-described embodiment and the accompanying drawings. The scope of rights of the present disclosure is defined by the appended claims, and the skilled person to the art may be obvious that various substitutes, modifications and changes may be made within the scope that does not deviate from the technical spirit of the present disclosure based on the claims.

The invention claimed is:

1. A microcurrent patch comprising:
   a base made of a polymer film;
   a small-sized battery disposed on the base to generate current;
   a circuit disposed on the base and connected to the small-sized battery, wherein the circuit are disposed in two regions so that the current flows in the circuit; and
   a glue layer having one face disposed on the base and constructed to cover the small-sized battery and the circuit, and having the other face attached to a skin of a human body, wherein the glue layer has a plurality of holes defined therein overlapping the circuit and served as a passage to allow the current to flow between the skin and the circuit when the patch is attached to the skin of the human body,
   wherein the circuit is electrically connected to the small-sized battery, the circuit is divided into a circuit portion connected to a positive terminal of the small-sized battery and a circuit portion connected to a negative terminal of the small-sized battery,
   the circuit is formed in a linear shape and crosses each other in a net shape so that current flows smoothly over a large area of the skin, and
   each of both opposing faces of the glue layer is made of acrylate and has insulation ability, and the glue layer has a thickness of 0.01 µm to 1,000 µm.

2. The patch of claim 1, wherein the base comprises one or more components from a group consisting of polyethylene naphthalate (PEN), and polyethylene terephthalate (PET).

3. The patch of claim 1, wherein the small-sized battery comprises at least two small-sized batteries arranged in a parallel manner and disposed on the base.

4. The patch of claim 1, wherein the small-sized battery comprises at least two small-sized batteries arranged in a series manner and disposed on the base.

5. The patch of claim 1, wherein a linear width of the linear shape is in a range of 0.01 to 10 mm.

6. The patch of claim 1, wherein the circuit comprises one or more components selected from a group consisting of carbon, nickel, silver, aluminum, copper, and gold.

* * * * *